US012778876B2

(12) United States Patent
Cushen

(10) Patent No.: US 12,778,876 B2
(45) Date of Patent: Nov. 3, 2026

(54) BIO-GEL COMPOSITION AND NAIL CARE SYSTEM

(71) Applicant: LILAQUE, INC., San Francisco, CA (US)

(72) Inventor: Julia D. Cushen, San Francisco, CA (US)

(73) Assignee: Lilaque Nails, LLC, Foster City, CA (US)

( * ) Notice: Subject to any disclaimer, the term of this patent is extended or adjusted under 35 U.S.C. 154(b) by 182 days.

(21) Appl. No.: 17/833,786

(22) Filed: Jun. 6, 2022

(65) Prior Publication Data

US 2022/0395449 A1 Dec. 15, 2022

Related U.S. Application Data

(60) Provisional application No. 63/196,999, filed on Jun. 4, 2021.

(51) Int. Cl.
*A61K 8/92* (2006.01)
*A61K 8/73* (2006.01)
*A61Q 3/02* (2006.01)

(52) U.S. Cl.
CPC ................ *A61K 8/92* (2013.01); *A61K 8/731* (2013.01); *A61Q 3/02* (2013.01); *A61K 2800/434* (2013.01)

(58) Field of Classification Search
None
See application file for complete search history.

(56) References Cited

U.S. PATENT DOCUMENTS

| | | | | | |
|---|---|---|---|---|---|
| 4,003,868 | A * | 1/1977 | Smith | B05D 3/0209 522/102 |
| 5,985,951 | A * | 11/1999 | Cook | C09D 101/10 522/89 |
| 2012/0190765 | A1* | 7/2012 | Chopra | C09D 5/037 522/78 |
| 2013/0146077 | A1* | 6/2013 | Cooke | A61Q 3/02 132/200 |
| 2013/0263875 | A1* | 10/2013 | Burgess | A61K 8/72 132/73 |
| 2015/0139924 | A1* | 5/2015 | Zhou | A61K 8/8164 424/61 |
| 2017/0226050 | A1* | 8/2017 | Voronov | C09D 133/24 |
| 2018/0194044 | A1 | 7/2018 | De Groot | |
| 2018/0214352 | A1* | 8/2018 | Takahashi | A61K 6/887 |
| 2020/0078288 | A1 | 3/2020 | Mannari et al. | |

FOREIGN PATENT DOCUMENTS

| | | | | |
|---|---|---|---|---|
| WO | WO-2004083327 A1 * | 9/2004 | C08F 251/02 |
| WO | WO-2016076662 A1 * | 5/2016 | B41J 11/002 |

OTHER PUBLICATIONS

Dianal "Viscosity Conversion Table," accessed 2023; https://j.b5z.net/i/u/2119873/i/data/viscosity.pdf (Year: 2023).*
Su et al. "One-step synthesis of novel renewable multi-functional linseed oil-based acrylate prepolymers and its application to UV-curable coatings," Progress in Organic Coatings 148:105820, 2020 (Year: 2020).*
Robert "Green ink in all colors—printing ink from renewable resources," Progress in Organic Coatings 78:287-292, 2015 (Year: 2015).*
Google translation WO 2016/076662, printed 2024 (Year: 2024).*
Jameson, "How hot does a typical hair dryer get?" published online Mar. 28, 2024; https://www.laifentech.com/blogs/news/how-hot-does-a-hair-dryer-get (Year: 2024).*
ASTM D7867, reapproved 2020; https://cdn.standards.iteh.ai/samples/107898/df42efc353ff4902b780dbc53c2ebfe1/ASTM-D7867-13-2020-.pdf (Year: 2020).*
Zareanshahraki, Forough, and Vijay Mannari. ""Green" UV-LED gel nail polishes from bio-based materials." International journal of cosmetic science 40.6 (2018): 555-564.

* cited by examiner

*Primary Examiner* — Bennett M Celsa
*Assistant Examiner* — Alissa Prosser
(74) *Attorney, Agent, or Firm* — BROOKS KUSHMAN P.C.

(57) ABSTRACT

A nail-care composition includes at least 50 wt. % bio-based components, based on the total weight of the composition, including acrylated epoxidized soybean oil and acrylated linseed oil as bio-based monomer(s) and/or oligomer(s) in a ratio of about 4:1 to 7:1, photoinitiator(s); and adhesion promoter(s), the composition having a shear-dependent viscosity of about 1200-4000 cP, measured according to ASTM D7867, under shear stress of about 10-180 $N/m^2$.

20 Claims, 3 Drawing Sheets

BIO-GEL COMPOSITION AND NAIL CARE SYSTEM

CROSS REFERENCE TO RELATED APPLICATIONS

This application claims the benefit of U.S. Application Ser. No. 63/196,999, filed Jun. 4, 2021, the disclosure of which is incorporated in its entirety by reference herein.

TECHNICAL FIELD

The present disclosure relates to a coating composition, a coating system, and methods of producing and using the same as a nail-care system.

BACKGROUND

Coating systems for nails are used to protect the nail surface and provide an attractive aesthetic appeal. People have long recognized nails as an indication of health. Accordingly, many people take nail care very seriously—providing routine maintenance, applying protective coatings, and/or applying attractive designs to their nails. Manicures and pedicures are common procedures for maintaining and providing fashionable designs to the nails of hands and feet.

Current coating systems such as nail polishes include solvent-based compositions, those curable by, for example, ultraviolet (UV) irradiation, or their combinations. Both systems involve an array of chemicals and chemical processes that may not be environmentally friendly or sustainable. Typically, solvent-based systems have shorter longevity (i.e., they do not last as long) and UV curable systems are difficult to remove. For example, solvent-based systems may start to chip after mere three to seven days, whereas UV curable systems may last for up to three weeks. But removal may be painful or uncomfortable. The removal process typically requires abrasive removal (e.g., rotary abrasion) and/or a solvent soak in, for example, acetone for up to 30 minutes. Because of these difficulties, beauty salons often apply and remove coating systems to nails. But at-home or do-it-yourself systems exist and are gaining popularity.

SUMMARY

In one or more embodiments, a nail-care composition is disclosed. The composition may include at least about 50 wt. % bio-based components, based on the total weight of the composition. The composition may include acrylated epoxidized soybean oil and acrylated linseed oil as bio-based monomer(s) and/or oligomer(s) in a ratio of about 4:1 to 7:1, photoinitiator(s), and adhesion promoter(s). The composition may have a shear-dependent viscosity of about 1200-4000 cP, measured according to ASTM D7867, under shear stress of about 10-180 N/m$^2$. The adhesion promoter(s) may be bio-based. The adhesion promoter(s) may include at least two different compounds. The at least two different compounds may be in a ratio of about 1:2 to 2:1. The photoinitiator(s) may include two different compounds in a ratio of about 3.5:1.5. The composition may also include a bio-based film former in an amount of about 1-10 wt. %, based on the total weight of the composition. The bio-based film former may include cellulose acetate butyrate having molecular weight of at least about 12 kg/mol. The composition may further include an accelerator in an amount of up to about 10 wt. %, based on the total weight of the composition.

In another embodiment, a nail-care composition is disclosed. The composition may include about 40-80 wt. % bio-based monomer and/or oligomer(s); about 15-30 wt. % adhesion promoter(s); and about 1-7 wt. % photoinitiator(s). The composition may be a thixotropic fluid. More than about 50 wt. % of the composition may be bio-based. The composition may have a shear-dependent viscosity of about 1200-4000 cP, measured according to ASTM D7867, under shear stress of about 10-180 N/m$^2$. The bio-based monomer and/or oligomer(s) may include vegetable/plant oil(s) having a glass transition temperature $T_g$ of about −15 to 35° C., measured according to ASTM D882. The adhesion promoter may be bio-based. The photoinitiator(s) may include two different compounds in a ratio of about 3.5:1.5. The composition of claim 9 may further include about 3-7 wt. % photoinitiator(s), 1-7 wt. % film former(s), 1-5 wt. % pigment(s), 1-10 wt. % accelerator(s), or a combination thereof, the weight % based on the total weight of the composition. The composition may have an impact resistance of at least about 40 in/lbs, as measured according to ASTM D2794.

In an alternative embodiment, a nail-care system is disclosed. The system may include a first thixotropic, predominantly bio-based composition, applicable onto a keratin-based substrate. The first composition may include about 50-70 wt. % bio-based monomer and/or oligomer(s) including vegetable and/or plant oils; about 15-30 wt. % adhesion promoter(s); and about 1-7 wt. % initiator(s). The system may have an impact resistance of at least about 40 in/lbs, as measured according to ASTM D2794 and longevity of at least 7 days. The system may further include a second thixotropic, predominantly bio-based composition, applicable onto the first composition after cure. The composition may include about 50-70 wt. % bio-based monomer and/or oligomer(s) including vegetable and/or plant oils; about 15-30 wt. % adhesion promoter(s); about 1-7 wt. % initiator(s); and about 1-7 wt. % accelerator(s). The system may further include a second thixotropic, predominantly bio-based composition free of a pigment, and wherein the first composition further comprises a pigment dispersion. The system may be substantially free of fossil-based components. The vegetable and/or plant oils may include acrylated linseed oil. The second composition may include at least one different initiator than the first composition.

In yet another embodiment, a nail care composition is disclosed. The composition may include about 30-95% by weight of a bio-based monomer and/or oligomer, about 1-30% by weight of a bio-based reactive diluent, about 1-30% by weight of additional monomers and/or oligomers, about 0.1-10% by weight of a pigment, about 0.1-7% by weight of a photoinitiator, and about 0.1-10% by weight of a bio-based plasticizer and/or film former. The nail care composition may be comprised of greater than about 50% bio-based ingredients by weight. Upon irradiation curing, the composition may form a cross-linked polymer network.

In one or more embodiments, a nail care coating system is disclosed. The system may include a basecoat layer, a color coat layer and a topcoat layer may be provided. The basecoat layer may include a crosslinked polymer network formed from a bio-based monomer and/or oligomer, and a bio-based reactive diluent with a bio-based plasticizer dispersed therein. The color coat layer may include a polymer network formed from a bio-based monomer and/or oligomer and a reactive diluent with a bio-based plasticizer, rheology modifier and pigment dispersed therein. The topcoat layer may include a crosslinked polymer network formed from a bio-based monomer and/or oligomer and a bio-based reactive diluent with a bio-based plasticizer dispersed therein. The coating system may be greater than 50% bio-based by weight.

DETAILED DESCRIPTION

Figure 1:
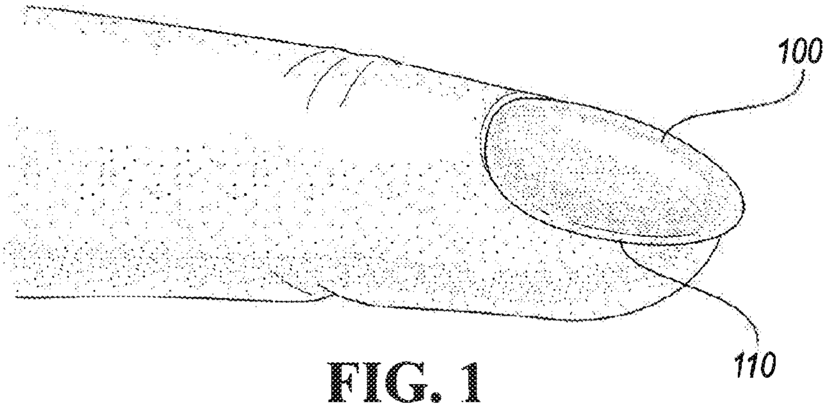
FIG. 1 is a schematic illustration of a sustainable coating system applied to a user's fingernail according to one or more embodiments disclosed herein.

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present embodiments. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Except in the examples, or where otherwise expressly indicated, all numerical quantities in this description indicating amounts of material or conditions of reaction and/or use are to be understood as modified by the word "about" in describing the broadest scope of the disclosure. Practice within the numerical limits stated is generally preferred. Also, unless expressly stated to the contrary: percent, "parts of," and ratio values are by weight; the description of a group or class of materials as suitable or preferred for a given purpose in connection with the disclosure implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "substantially," "generally," or "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the disclosure can be obtained within a range of +/−5% of the indicated value. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4, . . . , 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. Similarly, whenever listing integers are provided herein, it should also be appreciated that the listing of integers explicitly includes ranges of any two integers within the listing.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

As used herein, the term "and/or" means that either all or only one of the elements of said group may be present. For example, "A and/or B" means "only A, or only B, or both A and B". In the case of "only A," the term also covers the possibility that B is absent, i.e. "only A, but not B".

It is also to be understood that this disclosure is not limited to the specific embodiments and methods described below, as specific components and/or conditions may, of course, vary. Furthermore, the terminology used herein is used only for the purpose of describing particular embodiments of the present disclosure and is not intended to be limiting in any way.

The term "comprising" is synonymous with "including," "having," "containing," or "characterized by." These terms are inclusive and open-ended and do not exclude additional, unrecited elements or method steps. The term "including" or "includes" may encompass the phrases "comprise," "consist of," or "essentially consist of."

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed subject matter can include the use of either of the other two terms.

The term "one or more" means "at least one" and the term "at least one" means "one or more." The terms "one or more" and "at least one" include "plurality" as a subset.

The description of a group or class of materials as suitable for a given purpose in connection with one or more embodiments implies that mixtures of any two or more of the members of the group or class are suitable. Also, the description of a group or class of materials as suitable for a given purpose in connection with one or more embodiments implies that the group or class of materials can "comprise," "consist of," and/or "consist essentially of" any member or the entirety of that group or class of materials. First definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

Throughout history, people's interest in art, decorating, and attractive looks have resulted in development of various beauty technologies including application of nail art, polishes, artificial nails, etc. to enhance the look of one's nails. In time, it has also become important to provide beauty products, especially those directly applied to a human or animal body, having minimal toxicity and being environmentally friendly.

Currently, majority of the nail product lines utilize non-renewable resources. Additionally, many of the traditional nail polish components may cause allergic reactions, dermatitis, eye irritation, and even more serious health issues such as kidney and nervous system damage. Since nail beauty products are being used by many children, pregnant women, as well a large percentage of adult population, there is a strong need for development of safer and more environmentally-friendly nail beautification system.

Additionally, there is a demand for long-lasting nail care products which are easily applicable and removable. Currently, the long-lasting options include gels and acrylics. Both systems require extensive removal time and efforts, which may have long-lasting negative effects on the user's body. For example, the gel nails are removed by filing off the gel from the nails. The acrylic nails are removed by soaking the nails in acetone for about 20 minutes. Both acetone and physical removal are potentially harmful techniques.

Accordingly, there is a need for a gentler, more environmentally friendly and/or sustainable nail coating composition and system.

In one or more embodiments, a bio-based nail care and/or beautification system is disclosed. "Bio-based" may refer to where a material comes from. A bio-based material may be sourced from renewable resources, biomass, plants. "Bio-based" is in contrast to conventional plastics, for example, which are fossil-based and thus non-renewable. In general, bio-based materials are considered more sustainable than materials sourced from fossil fuels because fossil fuels have finite reservoirs, and processing and/or use can be more harmful to the environment. Bio-based materials may be predominantly sourced from plants. Predominantly sourced means that a majority by weight of the monomer or oligomer is sourced from plants. In at least one embodiment, bio-based may be defined as set forth in ISO 16128.

The nail care system may be environmentally sustainable, green, bio-based, bio-derived, eco-friendly, biodegradable, made from renewable resources, made from non-fossil fuels, fossil-fuel free, or a combination thereof. The nail care system may use at least about 50, 60, 70, 80, 90, 95, or 100 wt. % of components which are made from renewable resources. Majority of the components in the nail care system may be sustainable, green, bio-based, or a combination thereof.

The nail care system may include one or more compositions. The one or more compositions may be applied as one or more layers, at least two layers, or two or more layers. The layers may include a base coat, color coat, top coat or gloss coat, or a combination thereof. The system may thus be a one-coat system, two-coat system, or a three-coat system. Additional coats are contemplated. In one or more embodiments, the system may be a two-coat system having a first combined base and color coat and a second top coat. Each coat may be applied in one, two, three, or more layers. The term coat may thus encompass a layer or coating.

Each coat may have a specific composition which may be the same or different than other coats. For example, the one-coat may use a first composition. One or more layers of the one-coat composition may be applied to obtain a suitable thickness, suitable cure, and/or the desired aesthetic effect. Thus, the system may include a number of layers having the same composition. Alternatively, the composition of the one-coat may be applied, followed by an application of a second composition, different than the first composition, to achieve desired properties and/or appearance. The second composition may form a top or gloss coat. The second coat may differ from the first coat by at least one different component, by an amount of at least one component, or both. The first coat may include all of the components of the second coat and at least one additional component. The first and second coats may include at least some same and some different components and/or different amounts of the same components.

Figure 2A:
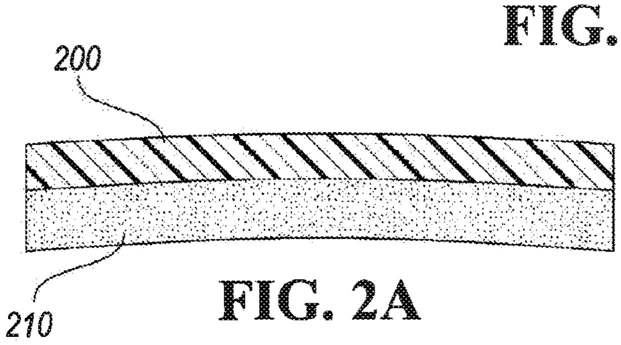
FIG. 2A is a schematic cross-section of a one-coat/one-layer coating system to a nail plate.
Figure 2B:
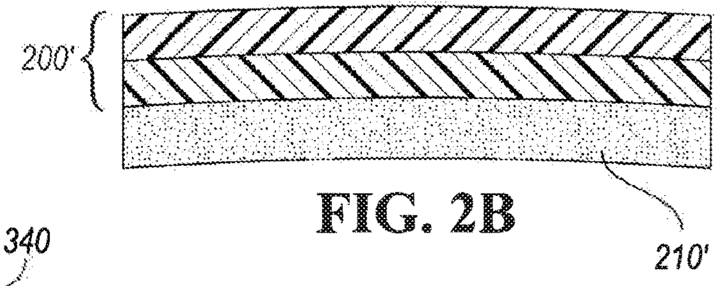
FIG. 2B is a schematic cross-section of a two-coat/two-layer coating system on a nail plate.

FIG. 1 provides a non-limiting example of a sustainable nail care coating system 100 on a user's fingernail 110. The system may have one or more layers, as described herein. FIG. 2A provides a schematic cross-section of a one-coat system 200 applied to a substrate 210. FIG. 2B provides a schematic cross-section of a two-coat system 200' applied to a substrate 210'.

Figure 3A:
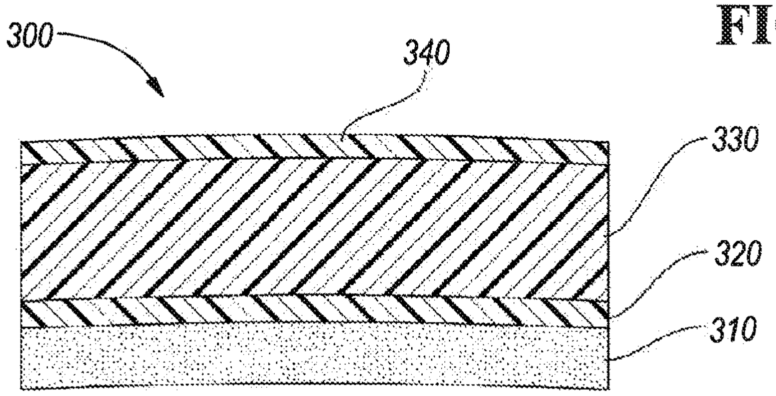
FIGS. 3A and 3B are schematic cross-sections of multi-coat/multi-layer coating systems or multi-step application to a nail plate.
Figure 3B:
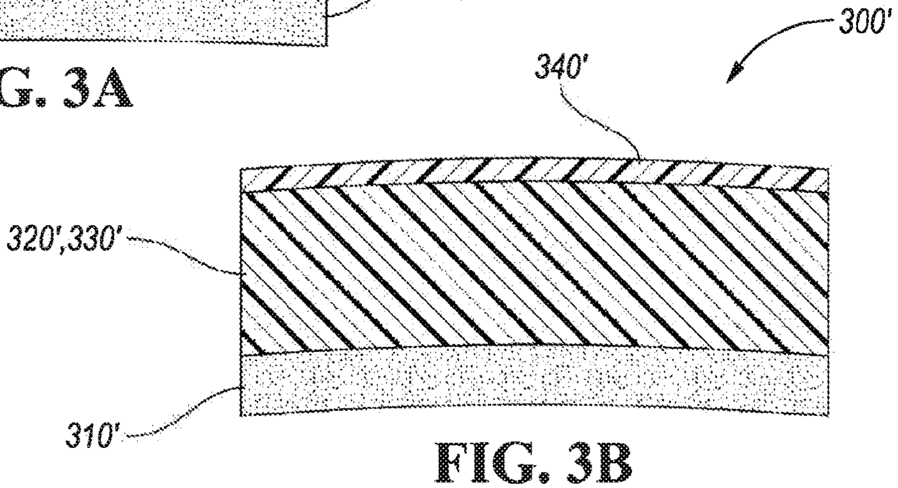
Figure 4:
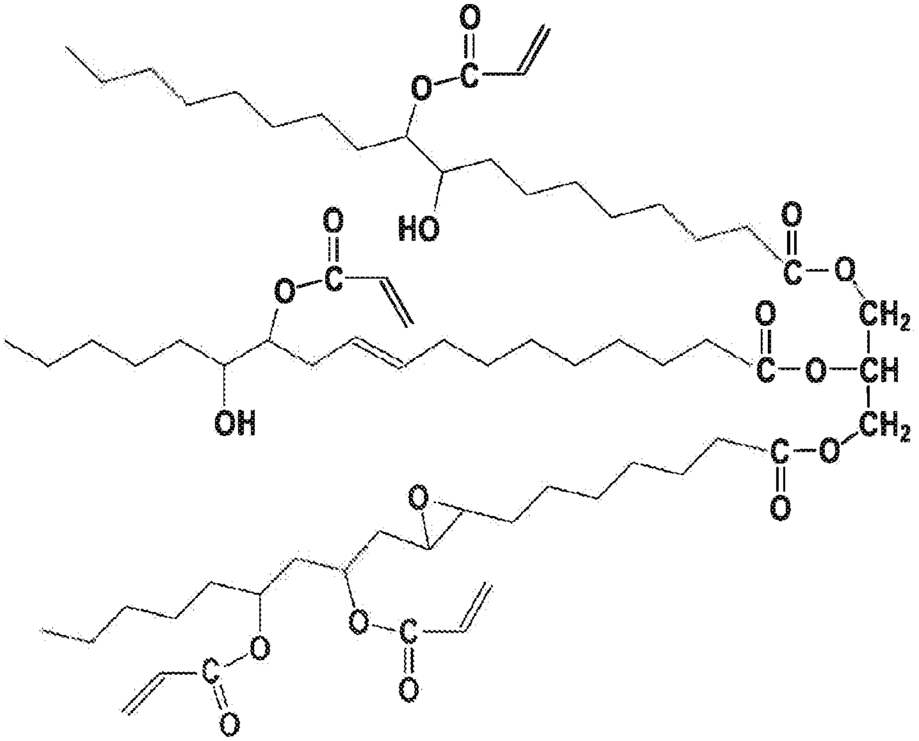
FIG. 4 is a schematic representation of an acrylated vegetable oil used in one or more compositions disclosed herein.

FIG. 3A provides a non-limiting example of a multi-coat coating system 300 such as a three-coat (i.e., 3-coat) nail polish coating system. The 3-coat coating system may include a basecoat layer 320, formed from curing a basecoat composition, on a nail plate or keratin surface 310. The 3-coat coating system may further include a color coat layer 330 formed from curing a color coat composition on the basecoat layer 320, and a topcoat layer 340 on the color coat layer 330, formed from curing a topcoat composition. In an alternative embodiment of FIG. 3B, the base coat and color coat layers of the system 300' are combined into a single layer 320', 330'.

When used for nail care, the system may be a nail polish and the substrate generally is a user's nail plate, a keratin-based surface, an artificial nail, nail extension, nail enhancement, etc. The coating system 100, 200, 200', 300 may also be applied to other coating layers or suitable surfaces.

The system includes a coating composition, which may include one or more components. The composition may include at least one or more optional components. The one or more components and the at least one or more optional components may be bio-based, green, sustainable, environmentally friendly, fossil-fuel free, or a combination thereof. At least some of the components may be bio-based, green, sustainable, environmentally friendly, fossil-fuel free, or a combination thereof. Some may mean one, two, three, four, or more components. Some may mean half of the components, more than half of the total number of components, at least half of the components by weight or volume, based on the total weight or volume of the composition of system, at least or up to about 25, 30, 35, 40, 45, 50, 55, 60, 65, 70, 75, 80, 85, 90, 95, or 99% of the components by weight or volume, based on the total weight or volume of the composition of system.

The composition may include at least one of (A) bio-based monomer(s) and/or oligomer(s), (B) bio-based reactive diluent(s), (C) initiator(s), (D) non-reactive additives such as a film former, a plasticizer, a rheology modifier, an adhesion promoter, a filler, (E) amine synergists, (F) pigment(s), (G) additional non-biobased components, (H) solvent, (I) accelerator, or a combination thereof. A single substance may function or be structured as one or more components of the composition. For example, the same chemical may be a reactive diluent as well as an adhesion promoter. In another non-limiting example, the same chemical may be a film former and a rheology modifier.

The nail care system disclosed herein may be activated or cured by temperature, UV, or another type of event matched to the type of initiator included in the system. Upon curing, for example, by exposure to radiation (e.g., UV light), the composition forms a hardened cross-linked polymer network with various components such as the non-reactive additives dispersed therein. Curing occurs through the polymerization of reactive components including (e.g., monomers and oligomers) via free radical polymerization. This type of polymerization begins when an initiator such as a photoinitiator forms free radicals after exposure to an initiating event such as temperature or UV exposure. The free radicals then react with reactive monomers and/or oligomers initiating a chain reaction that leads to polymerization.

The composition may include one or more (A) bio-based monomer(s) and/or oligomer(s) at about 30 to 95%, 45 to 85%, or 65 to 80% by weight of the total composition. The composition may include one or more (A) bio-based monomer(s) and/or oligomer(s) at about 30, 35, 40, 45, 50, 55, 60, 65, 70, 75, 80, 85, 90, or 95% by weight of the total composition. The bio-based monomer(s) and/or oligomer(s) provide functional properties of the system such as mechanical strength.

A bio-based monomer and/or oligomers may include compounds of various molecular weight with carbon-carbon double bonds that are suitable for free radical polymerization such as alkenes. The monomer and/or oligomer may be suitable for ultraviolent or electron beam curing. The bio-based monomer and/or oligomer may be one or more alkenes.

The bio-based monomer and/or oligomer may include acrylated vegetable and/or plant oil(s). A non-limiting example of the oil may be an oil derived from one or more portions of a plant such as the root, stem, flower, fruit, nut, and/or seed. A non-limiting example of the oil may include a linseed oil, flaxseed oil, rapeseed oil, castor seed oil, the like, or a combination thereof.

Non-limiting examples of the acrylated vegetable/plant oils may be acrylated linseed oil (ALO), acrylated epoxidized linseed oil (AELO), acylated soybean oil, acrylated epoxidized soybean oil (AESO), thiolene functionalized vegetable oils, and/or bio-based compounds with urethane dimethacrylates (UDMAs) or urethane diacrylate (UDAs) midsegments, the like, or a combination thereof. In a non-limiting example, ALO may be used, which has demonstrated good adhesion and mechanical properties. In another non-limiting example, AESO, may provide good adhesion which may be attributable to a relatively high concentration of hydrogen bonding.

The acrylated vegetable/plant oil(s) may have a relatively low glass transition temperature ($T_g$) of about −15 to 35° C., 0 to 20° C., or 5 to 10° C., as measure by ASTM D7028 or ASTM D882.

The acrylated vegetable/plant oil(s) may have multiple functional groups and/or multiple sites, per polymeric unit, structured to form hydrogen bonds with the nail plate and/or keratin. This principle is shown for example in a schematic depiction of an acrylated vegetable oil in FIG. 5. The acrylated vegetable/plant oil(s) may be characterized by triglycerides or fatty acids bonded together The bio-based monomer and/or oligomer may impart excellent impact resistance to the system. The bio-based monomer and/or oligomer may have a tensile strength of greater than about 500 PSI, 1000 PSI, or 1100 PSI, as measured by ASTM D638. The bio-based monomer and/or oligomer may have a tensile elongation of greater than about 5%, 10%, or 15%, as measured by ASTM D412.

The ratio of the bio-based monomer(s) and/or oligomer(s) may be 1:1, 2:1, 3:1, 4:1, 5:1, 6:1, 7:1, 8:1, 9:1, 2:3, 3:4, or the like. The ratio of the bio-based monomer(s) and/or oligomer(s) may be 1:1 to 9:1 or 4:1 to 7:1.

The coating composition may include one or more (B) bio-based reactive diluent(s) to achieve a suitable, predetermined viscosity of the composition. The monomers, and more specifically oligomers of (A), may be too thick or have too great a viscosity and may require the addition of a reactive diluent to lower the viscosity. Oligomers may have viscosities as high as 30,000-400,000 centipoise (cP).

The reactive diluent(s) may be used to lower viscosity of the composition to a predetermined value. The predetermined viscosity value of the composition may be about 100 to 10,000 cP, 1,000 to 7,000 cP, or 3,000 to 5,000 cP at shear rate of about 3 to 60, 5 to 50, or 8 to 40 $s^{-1}$. Viscosity may be measured, unless stated otherwise, for example, at 30° C. using a viscometer such as a Brookfield viscometer and a coaxial cylindrical spindle per ASTM D7867.

The composition may exhibit a shear-thinning rheology after overcoming a yield point. The reactive diluent(s) may be present at about 1 to 50%, 2 to 30%, or 3 to 10% by weight of the total composition. The reactive diluent(s) may be present at about 1, 2, 3, 4, 5, 8, 10, 12, 15, 17, 20, 22, 25, 27, 30, 32, 35, 37, 40, 42, 45, 47, or 50% by weight of the total composition.

At least some of the reactive diluent(s) may be environmentally sustainable, green, bio-based, bio-derived, eco-friendly, biodegradable, fossil-fuel free, or a combination thereof. At least 50 wt. % of all reactive diluent(s) may be environmentally sustainable, green, bio-based, bio-derived, eco-friendly, biodegradable, fossil-fuel free or a combination thereof.

The bio-based reactive diluents may be, for example, alkene monomers and/or small oligomers with lower viscosities such as viscosities of less than about 1,000 cP, 100 cP, or 10 cP, at a shear rate of 15 $s^{-1}$ or less. Reactive diluents may include monomers and/or oligomers with a viscosity between 1 to 10 cP.

The reactive diluents may have a molecular weight of less than about 5,000 g/mol, 1,000 g/mol, or 500 g/mol. Suitable bio-based reactive diluents may include, but are not limited to, isobornyl methacrylate (IBOMA), isobornyl acrylate (IBOA), lauryl acrylate (LA), tricyclodecanedimethanol diacrylate (TCDDA), monofunctional methacrylated monomer, the like, or a combination thereof. For example, IBOMA and IBOA may be derived from camphene which is derived from plants.

Additional reactive diluents which are not bio-based may be included in some embodiments due to solubility restraints.

The coating composition may include one or more (C) initiator(s) at about 0.1 to 10%, 2.5 to 7.5%, or 4 to 6% by weight of the total composition. The coating composition may include one or more (C) initiator(s) at about 0.1, 0.2, 0.5, 0.7, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, or 10% by weight of the total composition. An initiator such as a photoinitiator is included to initiate radical polymerization of unsaturated oligomers after exposure to UV. An initiator such as a photoinitiator is included to initiate the curing process by free radical polymerization.

The composition may include one or more types of initiators. The initiator may reduce oxygen inhibition and increase gloss in the coating. Eliminating or minimizing oxygen inhibition assists in obtaining suitable hardness and gloss. Oxygen inhibition refers to the process of a free radical binding with oxygen to form a less reactive component. This less reactive form results in a layer of unreacted or partially reacted monomers or oligomers. Under typical conditions, oxygen inhibition may form an oxygen inhibition layer of unreacted or partially reacted monomer/oligomers at the surface or the atmospheric interface due to the presence of oxygen in the air. Oxygen inhibition may reduce the efficiency of initiation, inhibit curing, reduce hardness, and/or reduce gloss. Thus, mitigating or eliminating oxygen inhibition is desirable. Hence, the chemical composition and/or concentration of one or more photoinitiators may be tuned to control the hardness and/or gloss of the final cured coating. The coating compositions with higher concentrations of photoinitiator may have less oxygen inhibition, for example, a concentration of greater than about 3 wt. %, 4.5 wt. % or 6 wt. %, based on the total weight of the composition, may have less oxygen inhibition.

An example initiator may absorb at a wavelength of about 330-500, 340-490, or 350-370 nm. Each coat may include a different initiator. For example, the top coat composition may include an initiator which absorbs at lower wavelength than an initiator in the base+color coat composition. Lower wavelengths may penetrate less into the film and thus generate a higher reaction activity at the surface which is desirable for the top coat. An example top coat initiator may absorb at a wavelength of about 330-400, 340-390, or 350-380 nm. An example base+color coat initiator may absorb at a wavelength of about 395-500, 400-490, or 405-485 nm.

Each coat may have the same type of initiator but differ in the amount or concentration of the initiator compound. For example, the first coat may have a lower concentration of initiator than the top coat to reduce the crosslink density contributing to delamination, potentially making removal easier. The top coat may have a greater concentration of the initiator than the underlying coats by about 3-10, 4-8, or 5-7 wt. %.

In a color coat of the three-layer/three-coat system, the concentration of the initiator may be at an amount that is in between the concentration used in the basecoat and topcoat compositions. This may provide for balance between mechanical properties and the ease of removal by providing a suitable crosslink density.

A non-limiting example of a photoinitiator may be a solid, a liquid, a gel, or a combination thereof. A non-limiting example of a photoinitiator may be diphenyl (2,4,6-trimethylbenzoyl)phosphine oxide (TPO), which is a solid, ethyl (2,4,6-trimethylbenzoyl)phenylphosphinate (TPO-L), a liquid, 2-hydroxy-2-methyl-1-phenylpropan-1-on, benzophenone, polymeric benzophenone, 1-[4-(2-hydroxyethoxy)-phenyl]-2-hydroxy-2-methyl-1-propane-1-one, 2-isopropylthioxanthone, 1-hydroxycyclohexyl phenyl ketone (HCPK), polymeric thioxanthone, trimethylolpropane ethoxylate triacrylate, 3-cyclopentyl-1-(4-(phenylthio) phenyl)propan-1,2-dione-2-(O-benzoyloxime), 1-[9-ethyl-6-(2-methylbenzoyl)-9H-carbazol-3-yl]-3-cyclopentylpropanone-1-(O-acetyloxime), bis(4-dodecylphenyl)iodonium hexafluoroantimonate, 4-isopropyl-4'-methyldiphenyliodonium tetrakis(pentafluorophenyl)borate, 2-methyl-1-[4-(methylthio)phenyl]2-morpholinopropan-1-one, (sulfanediyldibenzene-4,1-diyl)bis (diphenylsulfonium) bis(hexafluoroantimonate) in propylene carbonate, the like, or a combination thereof.

A surface-active photoinitiator may also be used to reduce oxygen inhibition such as, for example, HCPK. A surface-active photoinitiator may be used in combination with other initiators or provided in an initiator package. A common initiation event is exposure to irradiation at or near the UV spectrum. But various wavelengths and intensities may be used for initiation. For example, electromagnetic radiation with a wavelength in a spectrum of about 100 to 500 nm, 300-450 nm, or 350-410 nm may be used. Light, for example, with a wavelength of about 405 nm may be suitable for TPO and light at about 365 nm may be suitable for HCPK. The intensity or optical power may be about 1 to 100 $mW/cm^2$, 3 to 70 $mW/cm^2$, or 6 to 40 $mW/cm^2$.

In a non-limiting example, the top coat and the base+color coat may each include a photoinitiator which may absorb at a wavelength of 365, 385, and/or 405 nm. The top coat may additionally a second type of initiator. In a non-limiting example, the top coat may include HCPK at about 1.5 wt. % and TPO at about 3.5 wt. %. The base+color coat may include TPO at a concentration of about 5 wt. %.

The ratio of the first to second initiator in the top coat may be about 1:1, 1:2, 1:3, 1:4, 1:5, 1:6, 1:7, 2:3, 1.5:3.5, or the like.

The composition may also include one or more (D) non-reactive additives present, individually or in total, at about 0.01 to 70%, 1 to 35%, or 2 to 20% by weight of the total composition. The composition may also include one or more (D) non-reactive additives present, individually or in total, at about 0.01, 0.05, 0.1, 0.2, 0.5, 0.7, 1, 1.5, 2, 5, 7, 10, 12, 15, 17, 20, 22, 25, 27, 30, 32, 35, 37, 40, 42, 45, 47, 50, 52, 55, 57, 60, 62, 65, 67, or 70% by weight of the total composition. The one or more non-reactive additives may include one or more film formers, plasticizers, adhesion promoters, rheology modifiers, amine synergists, pigments, fillers, or a combination thereof. The non-reactive additive may include a bio-based, bio-derived, sustainable, green, environmentally friendly, fossil-fuel free component. All or at least one of the non-reactive additives may be bio-based, bio-derived, sustainable, green, environmentally friendly, fossil-fuel free component.

The term "non-reactive" additives refers to components that do not directly participate in the polymerization reaction or form a polymeric unit in the polymer network upon curing. Non-reactive additives may be trapped, dispersed, and/or distributed throughout the polymer network without being covalently bonded or forming an integral part of the polymer network. Non-reactive additives may impart desirable properties to the composition prior to curing and/or desirable properties to the final cured coating layer and/or system. Non-reactive additives may include film formers, bio-based plasticizers, rheology modifiers, and/or pigments. Non-reactive additives may adjust mechanical properties such as strength or hardness, modify rheology such as altering viscosity, dilute crosslink density, and/or promote swelling for removal via solvent soaking.

The composition may include one or more film formers, plasticizers, or both. A film former and/or plasticizer may be bio-based, bio-derived, sustainable, green, environmentally friendly. Film formers may contribute to various desirable properties such as improved adhesion and film formation. The film former and/or plasticizer may relax network density of the composition to improve mechanical properties, wet surface, balance the adhesion, assist with removal, or a combination thereof. The film former and/or the plasticizer may reduce the overall cross-link density per unit of volume. The film former and/or the plasticizer may increase the solubility of the coating system in a solvent, enabling easier removal. The film former may also be a rheology modifier at the same time or in the same application, composition, and/or system. A film former with an increased number of hydrogen bonding sites may impart good adhesive properties in compositions and in direct contact with the nail plate or keratin substrate.

In a non-limiting example, the film former and/or the plasticizer may be present at about 0.1 to 20%, 0.5 to 15%, or 0.8 to 10% by weight of the total composition. The film former and/or the plasticizer may be present at about 0.1, 0.2, 0.5, 0.7, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 10, 10.2, 10.5, 10.7, 11, 11.2, 11.5, 11.7, 12, 12.2, 12.5, 12.7, 13, 13.2, 13.5, 13.7, 14, 14.2, 14.5, 14.7, 15, 15.2, 15.5, 15.7, 16, 16.2, 16.5, 16.7, 17, 17.2, 17.5, 17.7, 18, 18.2, 18.5, 18.7, 19, 19.2, 19.5, 19.7, or 20% by weight of the total composition.

Preferably bio-based film formers may be used. Suitable film formers may include cellulose-based compounds such as cellulose acetate butyrate (CAB), nitrocellulose, polyvinyl butyral, polyacrylic acid (PAA), polylactic acid (PLA), polyhydroxyalkanoate (PHA), polyhydroxybutyrate (PHB), polybutylene succinate adipate (PBSA), polybutylene adipate/terephthalate (PBAT), the like, or their combination. A non-limiting example may be polyacrylic acid, CAB with a molecular weight of at least 10, 12, 14, 16, or 18 kg/mol may be used, or their combination.

Suitable bio-based plasticizers may include rosins, gum rosin, vegetable oils, soybean oil, castor oil, coconut oil, beeswax, saturated and unsaturated fatty acids, the like, or a combination thereof. Bio-based plasticizers may add flexibility and longevity. Bio-based plasticizers may also contribute to easier removal by diluting the other reactive components. Bio-based plasticizers, acting as a small molecule intermediate, may also enable easier removal by providing a soluble or more soluble component at the nail plate-film interface.

The composition may include one or more rheology modifiers. The rheology modifiers may be used to provide a suitable rheology and/or viscosity for stabilizing pigment and other solid components in the composition. Rheology modifiers may also provide suitable leveling characteristic and assist in preventing pooling in the lateral folds of the fingers or toes.

The rheology modifier may be present at about 0.1 to 20%, 0.5 to 15%, or 0.8 to 10% by weight of the total composition. The rheology modifier may be present at about 0.1, 0.2, 0.5, 0.7, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 10, 10.2, 10.5, 10.7, 11, 11.2, 11.5, 11.7, 12, 12.2, 12.5, 12.7, 13, 13.2, 13.5, 13.7, 14, 14.2, 14.5, 14.7, 15, 15.2, 15.5, 15.7, 16, 16.2, 16.5, 16.7, 17, 17.2, 17.5, 17.7, 18, 18.2, 18.5, 18.7, 19, 19.2, 19.5, 19.7, or 20% by weight of the total composition.

The rheology modifiers may provide for a shear-thinning rheology which is suitable for pigment stabilization, even color coat, and/or extended shelf-life. The rheology modifiers may keep viscosity within a desired, predetermined working range. The working range is determined such that the composition forms an even coating once applied onto a substrate. The rheology modifiers may be organic or inorganic. The rheology modifiers may be bio-based, bio-derived, sustainable, green, environmentally friendly. A rheology modifier may be also a film former at the same time, in the same application, coating, composition, system.

The basecoat composition may have no rheology modifier because a thin composition and/or coating layer may be desirable. Without a rheology modifier, the basecoat composition may have a Newtonian rheology or more Newtonian rheology. The composition may exhibit a shear-thinning rheology after overcoming a yield point.

The desirable viscosity of the composition may be above 700, 750, 800, 850, 900, 950, 1000, 1050, 1100, 1150, 1200, 1250, or 1300 cP under shear stress of about 10-180 $N/m^2$, shear stress of about 3-40 1/s, or both as the viscosities below the one or more of the named numerals may result in difficult application of the coating onto the substrates named herein. The final sheer-dependent viscosity may be about 1200 to 4500, 1300 to 4250, or 1500 to 4000 cP under shear stress of about 10-180 $N/m^2$, shear stress of about 3-40 1/s, or both.

The composition may be a thixotropic fluid or one that takes a fixed time to return to its equilibrium viscosity when subjected to abrupt changes in shear rate. The composition may become less viscous, thinner or flows more easily, when shaken, stirred, agitated, or otherwise stressed.

Example viscosities under shear stress and shear rates of the compositions disclosed herein are shown in Tables 1 and 2 for the based+color coat and top coat, respectively. The measurements were conducted on a rheometer according to an RPM noted in the tables below at a temperature of 30° C., measurement time was 30 s.

TABLE 1

Color + based coat rheology table

| RPM | Viscosity [cP] | Shear Stress [N/m$^2$] | Shear Rate [1/s] |
|---|---|---|---|
| 15 | 3062 | 176.0 | 57.6 |
| 10 | 3164 | 122.0 | 38.4 |
| 5 | 3451 | 66.3 | 19.2 |
| 4 | 3558 | 54.7 | 15.4 |
| 3 | 3686 | 42.5 | 11.5 |
| 2 | 3968 | 30.5 | 7.68 |
| 1 | 4659 | 17.9 | 3.84 |
| 2 | 3968 | 30.5 | 7.68 |
| 3 | 3669 | 42.3 | 11.5 |
| 4 | 3507 | 53.9 | 15.4 |
| 5 | 3441 | 66.1 | 19.2 |
| 10 | 3210 | 123.0 | 38.4 |
| 15 | 3041 | 175.0 | 57.6 |

TABLE 2

Top coat rheology table

| RPM | Viscosity [cP] | Shear Stress [N/m$^2$] | Shear Rate [1/s] |
|---|---|---|---|
| 15 | 1103 | 63.50 | 57.6 |
| 10 | 1132 | 43.50 | 38.4 |
| 5 | 1147 | 22.00 | 19.2 |
| 4 | 1139 | 17.50 | 15.4 |
| 3 | 1126 | 13.00 | 11.5 |
| 2 | 1126 | 8.65 | 7.68 |
| 1 | 1075 | 4.13 | 3.84 |
| 2 | 1126 | 8.65 | 7.68 |
| 3 | 1126 | 13.00 | 11.5 |
| 4 | 1139 | 17.50 | 15.4 |
| 5 | 1147 | 22.00 | 19.2 |
| 10 | 1147 | 44.00 | 38.4 |
| 15 | 1150 | 66.30 | 57.6 |

The color coat, the base coat, or a combination thereof may have the greatest thickness of all the layers. The rheology modifier may contribute to the suitable thickness. A shear-thinning and/or thixotropic rheology also provides for pigment stabilization and leveling—without pooling in the lateral folds.

Suitable rheology modifiers may include fumed silica, modified fumed silicas, modified silicas, functionalized fumed silicas, natural clays such as bentonite or hectorite, cellulose-based polymers such as CAB, the like, or a combination thereof. Natural clays may be organically modified such as by cation exchange with a quaternary ammonium compound.

The composition may include one or more adhesion promoters. The adhesion promoter may be added to enhance adhesion of the composition to the substrate. The adhesion promoter may be present at about 1 to 30%, 2 to 20%, or 5 to 15% by weight of the total composition. The adhesion promoter may be present at about 1, 2, 5, 7, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30% by weight of the total composition. Example adhesion promoters may include pyromellitic dianhydrate dimethacrylate (PMDM), 2-hydroxypropyl methacrylate (HPMA), or their combination. The PMDM and HPMA may be in included in a ratio of 1:2, 1:3, 1:4, 1:5, 1:6, 1:7, 2:3 of PMDM:HPMA or HPMA:PMDM. The PMDM and HPMA may be in included in a ratio of about 2:1 to 1:2 of PMDM:HPMA or HPMA:PMDM.

The composition may include one or more fillers. The fillers may reduce cost and/or modify the mechanical properties of the composition and/or system such as strength or hardness. For example, a glass fiber may be used in one or more embodiments and may contribute to improved strength. Glass fiber may be present in the composition at about 0.1 to 50%, 1 to 30%, or 3 to 20% by weight of the composition. A non-limiting example of glass fiber may include borosilicate micro glass. The composition may be free of a filler.

The composition may include one or more (E) amine synergists. The amine synergist may be added to achieve gloss of the coating. An amine synergist may also be used to improve or speed the cure of the various compositions disclosed herein. The amine synergist may be used at about 0.1 to 10%, 0.5 to 7.5%, or 1 to 5% by weight of the total composition. The amine synergist may be used at about 0.1, 0.2, 0.5, 0.7, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, or 10% by weight of the total composition. The composition may be free of an amine synergist. The amine synergist may be a reactive component. The amine synergist may be a part of the top coat, color coat, based coat, or their combination. The amine synergist may be a part of the top coat only.

Non-limiting example amine synergists may include aminobenzoate, 2-ethylhexyl-4-(dimethylamino)benzoate, 2-(dimethylamino)ethylbenzoate, 2-butoxyethyl 4-(dimethylamino)benzoate, triethanolamine, the like, or a combination thereof. An amine synergist may be used in the top coat while being omitted in the base, color, or base+color coats as an amine synergist may not be compatible with pigments.

The composition may include one or more (F) pigments. The pigment(s) may add coloring to the composition. The pigment(s) may be present at about 0.1 to 30%, 0.5 to 10%, or 1 to 5% by weight of the total composition. The pigment(s) may be present at about 0.1, 0.2, 0.5, 0.7, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 10, 10.2, 10.5, 10.7, 11, 11.2, 11.5, 11.7, 12, 12.2, 12.5, 12.7, 13, 13.2, 13.5, 13.7, 14, 14.2, 14.5, 14.7, 15, 15.2, 15.5, 15.7, 16, 16.2, 16.5, 16.7, 17, 17.2, 17.5, 17.7, 18, 18.2, 18.5, 18.7, 19, 19.2, 19.5, 19.7, 20, 20.2, 20.5, 20.7, 21, 21.2, 21.5, 21.7, 22, 22.2, 22.5, 22.7, 23, 23.2, 23.5, 23.7, 24, 24.2, 24.5, 24.7, 25, 25.2, 25.5, 25.7, 26, 26.2, 26.5, 26.7, 27, 27.2, 27.5, 27.8, 28, 28.2, 28.5, 28.7, 29, 29.2, 29.5, 29.7, or 30% by weight of the total composition. The composition may be free of a pigment.

The pigment(s) may be bio-based, biodegradable, mineral-based, fossil-fuel free, or a combination thereof. The pigment(s) may include one or more minerals, micas. The pigment(s) may include one or more effect pigments such as bio-based glitter. The pigment(s) may be non-reactive.

The pigment or pigments may provide color or a desired aesthetic effect. In at least some embodiments a suitable pigment will comply with FDA regulations. The pigment may have a modified surface or be coated for easier dispersion such as with isopropyl titanium triisostearate. The pigment may also have a bio-based surface treatment. The pigment may be pre-milled preferably in a suitable monomer, oligomer, reactive diluent (e.g., AESO or IBOMA), and/or bio-based plasticizer to form a dispersion of the desired particle size before incorporation into the composition. Various additives may also be included to assist with a dispersion. Non-limiting examples include dispersing agents, wetting agents, and/or surfactant.

Non-limiting example pigments may include, but are not limited to, aluminum powder, iron oxides, mica, zinc oxide, or titanium dioxide. The pigment may also be a pigment lake such as, for example, a Red 7 Lake color additive. Non-limiting example pigments may include isonomyl isononanoate, ozokerite, polyhydroxystearic acid, the like, or a combination thereof.

The composition may also include one or more (G) additional components. The additional components may be non-biobased. The non-biobased components may include monomers/oligomers, reactive diluents, and/or an adhesion promoters. One or more of the additional components may be structured as a reactive diluent and an adhesion promoter. The individual or total weight of additional components may be about 1 to 30%, 1 to 20%, or 5 to 15% by weight of the total composition. The individual or total weight of additional components may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight of the total composition. The composition may have only a single type of additional components present.

Figure 5:
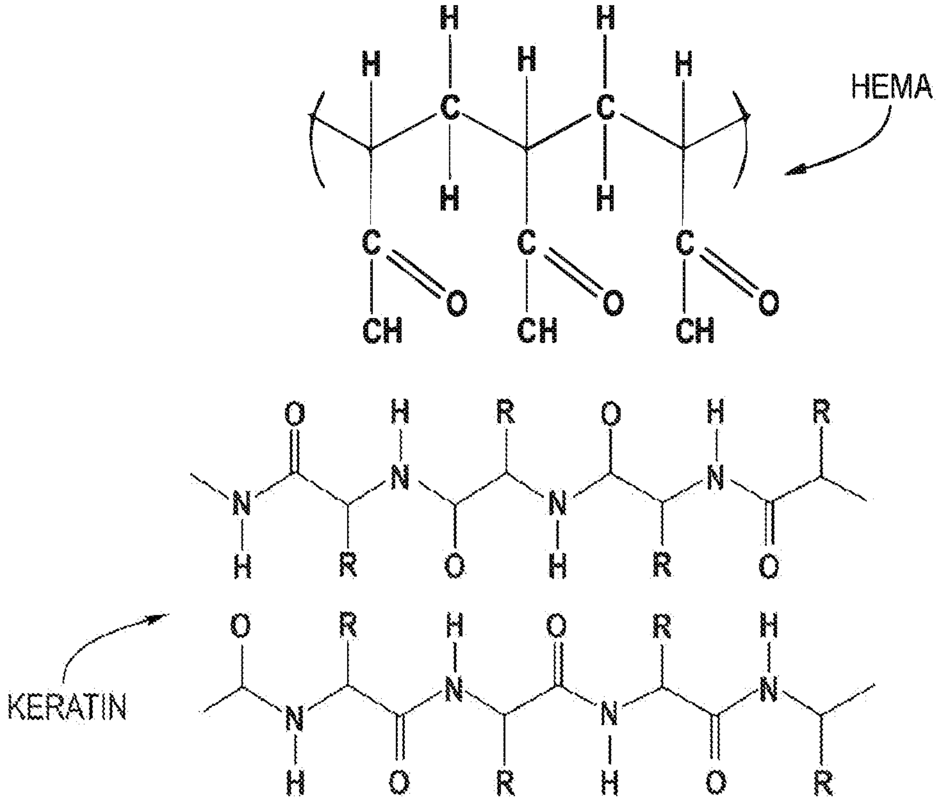
FIG. 5 is a schematic representation of the adhesive mechanism associated with hydroxyethyl methacrylate (HEMA)

Additional monomers and/or oligomers or adhesion promoters that may or may not be bio-based may be used to provide or supplement the final properties of the coating layer such as, for example, adhesion. Non-limiting examples of additional monomers and/or oligomers or adhesion promoters may include hydroxyethyl methacrylate (HEMA), hydroxy propyl methacrylate, HEMA phosphate, HEMA maleate, HEMA succinate, pyromellitic dianhydride glycerol (PMDM), urethane(meth)acrylate oligomers, and lauryl methacrylate (LMA), the like, or a combination thereof. This component may be most suitable in compositions that will come into direct contact with the nail plate or keratin-based substrate such as a one-layer or one-coat composition or basecoat composition. A mechanism of improving adhesion via HEMA is depicted in FIG. 5. FIG. 5 depicts hydrogen bonding the HEMA's $OH^-$ groups and the —NH groups in keratin.

The composition may be HEMA-free. Instead of HEMA, the composition may include one or more alternative additional monomers and/or oligomers or adhesion promoters. For example, the composition may include a combination of pyromellitic dianhydrate dimethacrylate (PMDM) and 2-hydroxypropyl methacrylate (HPMA). The PMDM and HPMA may be in included in a ratio of 1:2, 1:3, 1:4, 1:5, 1:6, 1:7, 2:3 of PMDM:HPMA or HPMA:PMDM.

The composition may also include one or more (H) solvents. The solvent may be included to dilute crosslinking and contribute to delamination for easier removal. The composition may include solvent at about 0.1 to 95%, 0.5 to 75%, or 1 to 50% by weight of the total composition. The composition may be free of a solvent.

Non-limiting examples of solvents include ethyl acetate, butyl acetate, acetone, isopropyl alcohol, the like, or their combination.

The composition may also include one or more (I) accelerators. The accelerator may be included to increase the speed of chemical reactions between components of the composition, system, promote surface cure, or a combination thereof. The composition may include accelerator at about 0.1 to 10%, 0.5 to 5%, or 0.75 to 1.5% by weight of the total composition. The composition may include accelerator at about 0.1, 0.2, 0.5, 0.7, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, or 10% by weight of the total composition. The composition may be free of an accelerator.

Non-limiting examples of accelerators include triethanolamine, 2-ethylhexa-4-dimethyalminobenzoate, the like, or a combination thereof.

The composition may be substantially free or free of one or more components (A), (B), (C), (D), (E), (F), (G), (H), (I). Practically, the composition may be free of one or more of (B), (E), (F), (G), (H), (I) compounds. For example, the composition may be free or substantially free of an amine synergist, a pigment, a rheology modifier, fillers, additional non-biobased components, accelerator, reactive diluent, and/or solvent. Substantially free means the composition contains less than about 5, 3, 4, 2, 0.5, or 0.1% by weight of a component.

A nail care system composition described herein may form a film. The film thickness may be about 25 to 700 μm, 50 to 500 μm, or 100 to 300 μm. For example, the film thickness may be applied at about 200 μm. As was stated above, multiple layers of the same composition may be applied and cured to achieve the desired film thickness or aesthetic affect. The film thickness refers to the aggregate film thickness of all the coating layers of the same or different compositions. For example, two 100 μm coatings of the same or different compositions may be considered to have a film thickness of 200 μm. The basecoat layer may have a film thickness of about 1 to 200 μm, 10 to 100 μm, or 25 to 75 μm. For example, the film thickness may be about 50 μm. The color coat layer may be applied at a film thickness of about 50 to 500 μm, 100 to 300 μm, or 150 to 250 μm. In a non-limiting example, the color coat film thickness may about 200 μm. As was stated above, the application of the color coat layer may include an application of the color coat composition multiple times to achieve the desired thickness and effect.

Each layer may have the same or different thickness. For example, the base+color coat, including one or more layers, may have the greatest thickness. The top coat may have the smallest thickness.

As was stated above, the system may include the same composition in each layer. Alternatively, the system may include at least two different compositions, each being specific to the type of coat.

The base coat, the color coat, or their combination may include a composition having, comprising, consisting of, or essentially consisting of one or more of or one or more of each of (A) bio-based monomer and/or oligomer, (B) a bio-based reactive diluent, (C) an initiator, (E) amine synergists, (F) pigment(s), and one or more (D) non-reactive additives named above. The basecoat, the color coat, or their combination may also include one or more (G) additional non-biobased component, (H) solvent, (I) accelerator, or a combination thereof.

The basecoat composition may have a lower concentration of bio-based ingredients than the top coat due to its unique role in adhesion and removal. Accordingly, the bio-based ingredients in the basecoat, color coat, or their combination, may be present at about 40 to 99%, 50 to 90%, or 60 to 85% by weight of the total composition. The top coat and the base+color coat composition may have the same amount of bio-based components.

The topcoat composition may include all of the components (A)-(I). Alternatively, the top coat composition may include a (A) bio-based monomer and/or oligomer, a (B) bio-based reactive diluent, an (C) initiator, and one or more (D) non-reactive additives. For example, the top coat composition may be free of a pigment, rheology modifier, filler, amine synergist, solvent, accelerator, or their combination. The topcoat composition may have no rheology modifier because a thin composition and/or coating layer may be desirable. Without a rheology modifier, the basecoat composition may have a Newtonian rheology or more Newtonian rheology. The top coat may further differ from the first coat by the type and/or amount of initiator. The topcoat composition may include a higher concentration of initiator, and or include a combination of initiators to improve process and composition properties such as minimize oxygen inhibition, increase hardness and/or improve gloss. The top coat may be free of a film former which may be present in the base+color coat. The base+color coat may be free of an accelerator, which may be included in the top coat.

The system may have good adhesion, superior toughness, gloss, good water resistance, high abrasion resistance, and suitable crosslink densities. The system may provide an impact resistance of greater than or at least about 20 in/lbs, 30 in/lbs, or 40 in/lbs, as measured by ASTM D2794. More than one parameter, or a set of parameters, may affect the gloss. As such, without limiting the disclosure to a single theory, it is believed that not one component, but a combination of components results in the desirable properties of the composition and/or system disclosed herein. The resulting composition may form a microstructure yielding a desirable, long-lasting gloss.

The system disclosed herein may have a conversion after cure of at least about 90, 91, 92, 93, 94, 95, 96, 97, 98, or 99%. A relatively high conversion rate, above 90%, means that the cured coating is less likely to change over time (i.e. curing more in sunlight/dark cure over time after the light is removed). A desirable conversion above 90% typically results in good mechanical properties and good adhesion by ensuring that the free monomer is incorporated. Additionally, a conversion rate above about 90% is an indicator of safety for the user from an allergy/sensitization perspective because a higher conversion means that the component which may cause allergy, the acrylate groups, have reacted as much as was feasible. It is believed that a relatively low conversion below about 90% could potentially mean presence of free unreacted monomers migrating and absorbing into the user's nail.

Figure 6:
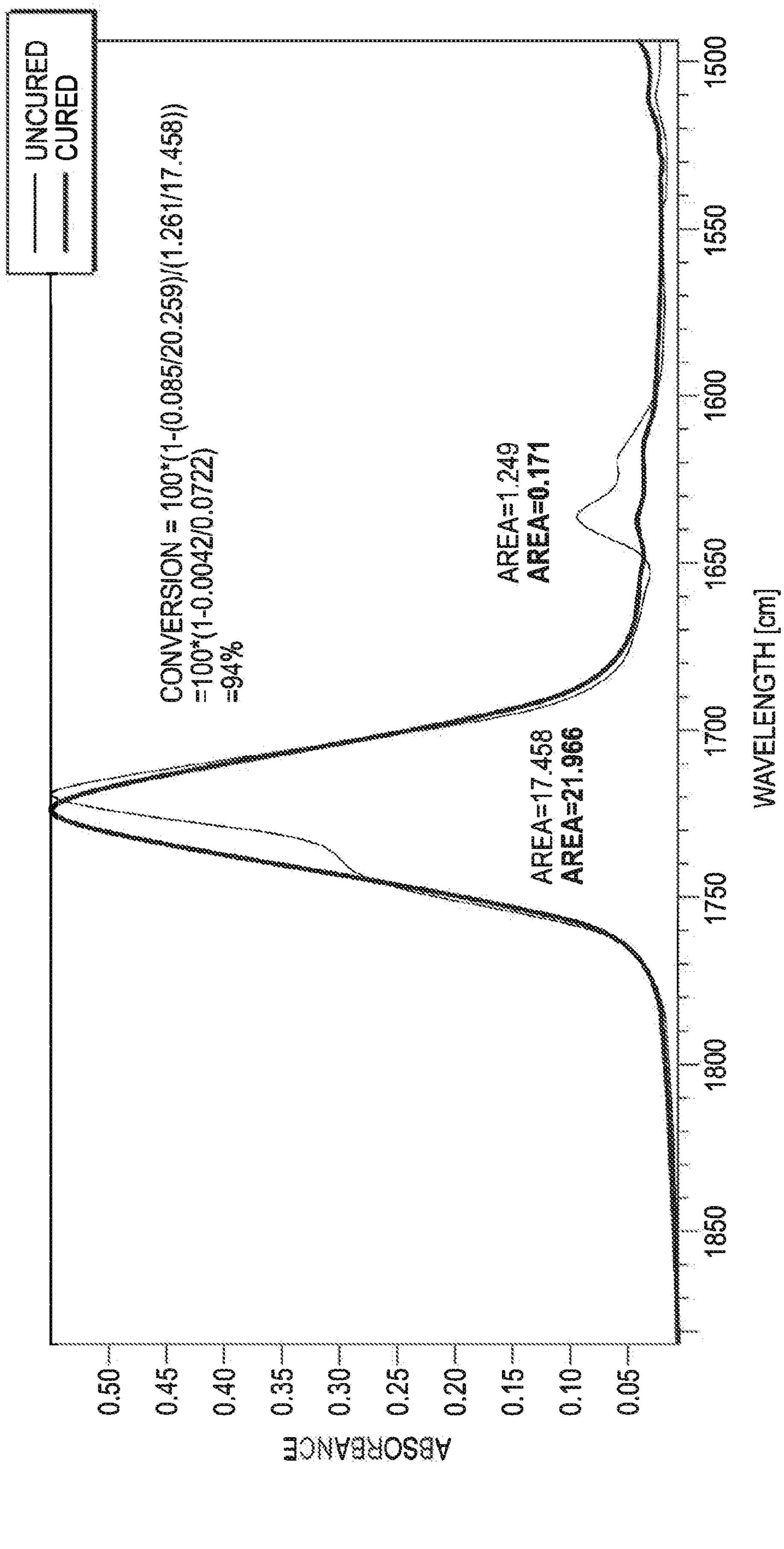
FIG. 6 is a conversion after cure plot of the one or more compositions disclosed herein.

The compositions disclosed herein were tested using ATR (attenuated total reflectance) measurement to assess the conversion percentage. The results can be seen in FIG. 6. The measured samples were coated on a glass slide at 100 μm thick and cured under a UV lamp to simulate a coating of the composition on a user's nail. The underside of the formed film was measured with FTIR to simulate conversion on the nail. Each sample rested for 24 h after cure. Conversion was calculated by measuring FTIR for an uncured and cured sample. Both spectra were normalized to the area under the curve for the carbonyl peak at 1720 cm-1 and either compared to how much the relative area under the 1637 cm-1 or 810 cm-1 acrylate peaks were left after cure. The results are shown in FIG. 6.

In one or more embodiments, a method of preparing the one or more compositions is disclosed herein. The method may include mixing all desirable components together to form the composition. The method may include pre-dissolving and/or pre-dispersing one or more individual components such as the pigments, rheology modifiers, or both. The method may include adding all the desirable components together. The method may include mixing/blending all the components for a period of time. The time period may differ and be for example 5 min to 1 hour, 10 to 45 min, or 15 to 30 min.

In one or more embodiments, a method of applying the composition(s) and/or system is disclosed herein. The method may include preparing the substrate surface. The method may include buffing and cleaning the substrate surface. If a prior coating system must be removed, an abrasive and/or chemical soak-off may be used to remove the previous coating system. Buffing generally involves creating a rougher surface to increase surface area. A fine grit buffer or 150 to 300 grit such as 240 grit may be used. The surface is then cleaned with a solvent such as with an acetone wipe to remove debris, particulate, and/or oils. After being buffed and cleaned, the composition may be applied to the substrate.

The method may include applying the composition by brushing, spraying, shaping, pressing, the like, or a combination thereof, onto the substrate. The method may include applying the composition in one or more layers. The method may include applying one or more compositions in one or more layers to achieve desirable thickness, look, gloss, strength, or a combination thereof. The method may include preventing pooling in lateral folds and application on the skin, which may lead to defects such as lifting, reduction of longevity, and/or sensitization.

The method may include curing the applied composition once or more times. The method may include applying a single layer/coat followed by curing the single layer/coat. The method may include curing the applied composition after each coat and/or layer is applied onto the substrate or the previously applied layer/coat. The method may include forming a hardened cross-linked coating layer by being exposed to light at or near the UV spectrum and allowing sufficient time (e.g., typically 2 minutes or less) for the polymerization to occur. The method may include, after curing, cleaning the coating with a solvent such as an isopropyl alcohol (WA) or an IPA wipe, but another organic solvent may be used.

The method may include repeating one or more steps disclosed herein. The method may include repeating applying, curing, cleaning, or a combination thereof until the entire system is applied and cured.

EXAMPLES

Examples 1-10

Examples 1-10 were prepared in the following manner. A pre-dispersed pigment, when present, was prepared first. The rheology modifier, when present, was pre-dissolved prior to its addition into the mixture. The individual components named in the Tables were added together. All of components were well incorporated into the mixture to facilitate compatibility and avoid agglomerations and/or bubbles from forming. Once added together, the components were mixed in a high dispersion mixer for about 1 to 30 minutes or until a suitable dispersion was obtained. The compositions had a viscosity of about 4,000 cP at a shear rate of 12.6 $s^{-1}$ and a shear-thinning rheology after overcoming the yield point. Examples 1 and 2 are general examples describing components and working ranges generally. Examples 3-10 provide specific component names and amounts.

TABLE 3

A general non-limiting example composition of Example 1

| Component | Amount [wt. %] |
|---|---|
| Bio-based monomer and/or oligomer(s) | 30-90 |
| Bio-based reactive diluent(s) | 1-30 |
| Adhesion promoter(s) | 2-25 |
| Additional reactive diluent(s) | 0-30 |
| Initiator(s) | 0.1-7 |

TABLE 3-continued

| A general non-limiting example composition of Example 1 | |
|---|---|
| Component | Amount [wt. %] |
| Bio-based plasticizer and/or film former(s) | 0.1-10 |
| Pigment(s) | 0-10 |
| Rheology Modifier(s) | 0-10 |
| Amine Synergist(s) | 0-5 |

TABLE 4

| A general non-limiting example composition of Example 2 | |
|---|---|
| Component | Amount [wt. %] |
| Bio-based monomer and/or oligomer(s) | 50-70 |
| Adhesion promoter(s) | 15-30 |
| Bio-based reactive diluent(s) | 0-15 |
| Photoinitiator(s) | 1-7 |
| Rheology modifier(s) and/or film former(s) | 0-7 |
| Pigment(s) | 0-7 |
| Accelerator(s) | 0-7 |

TABLE 5

| A non-limiting example composition of Example 3 | |
|---|---|
| Component | Amount [wt. %] |
| Acrylated epoxidized soybean oil (AESO) | 72 |
| Hydroxyethyl methacrylate (HEMA) | 10 |
| Lauryl acrylate (LA) | 5 |
| Castor oil | 5 |
| Red 7 lake pigment | 1 |
| diphenyl (2,4,6-trimethylbenzoyl)phosphine oxide (TPO) | 5 |
| Modified silica | 2 |

TABLE 6

| A non-limiting example composition of Example 4 | |
|---|---|
| Component | Amount [wt. %] |
| Acrylated epoxidized soybean oil (AESO) | 71 |
| Hydroxyethyl methacrylate (HEMA) | 10 |
| Lauryl acrylate (LA) | 5 |
| Castor oil | 5 |
| Cellulose Acetate Butyrate 12 kg/mol | 1 |
| Red 7 lake pigment | 1 |
| diphenyl (2,4,6-trimethylbenzoyl)phosphine oxide (TPO) | 5 |
| Modified silica | 2 |

TABLE 7

| A non-limiting example composition of Example 5 | |
|---|---|
| Component | Amount [wt. %] |
| Acrylated epoxidized soybean oil (AESO) | 58.5 |
| Hydroxyethyl methacrylate (HEMA) | 15 |
| Lauryl acrylate (LA) | 15 |
| Castor oil | 2.4 |
| Cellulose Acetate Butyrate 12 kg/mol | 3 |
| Red 7 lake pigment | 0.6 |
| diphenyl (2,4,6-trimethylbenzoyl)phosphine oxide (TPO) | 5 |
| Modified silica | 0.5 |

TABLE 8

| A non-limiting example composition of Example 6 - base + color coat | |
|---|---|
| Component | Amount [wt. %] |
| Acrylated epoxidized soybean oil (AESO) | 58 |
| Hydroxyethyl methacrylate (HEMA) | 20 |
| Acrylated linseed oil (ALO) | 10 |
| Diphenyl (2,4,6-trimethylbenzoyl)phosphine oxide (TPO) | 5 |
| Cellulose acetate butyrate (CAB, 12 kg/mol) | 3 |
| Pigment dispersion | 4 |

TABLE 9

| A non-limiting example composition of Example 7 - top coat | |
|---|---|
| Component | Amount [wt. %] |
| Acrylated epoxidized soybean oil (AESO) | 60 |
| Hydroxyethyl methacrylate (HEMA) | 20 |
| Acrylated linseed oil (ALO) | 10 |
| Triethanolamine | 5 |
| Diphenyl (2,4,6-trimethylbenzoyl)phosphine oxide (TPO) | 3.5 |
| 1-hydroxycyclohexyl phenyl ketone (HCPK) | 1.5 |

TABLE 10

| Non-limiting example of base + color coat composition of Example 8 | |
|---|---|
| Component | Amount [wt. %] |
| Acrylated epoxidized soybean oil (AESO) | 60 |
| Pyromellitic dianhydrate dimethacrylate (PMDM) | 10 |
| 2-hydroxypropyl methacrylate (HPMA) | 10 |
| Acrylated linseed oil (ALO) | 10 |
| Diphenyl (2,4,6-trimethylbenzoyl)phosphine oxide (TPO) | 5 |
| Cellulose acetate butyrate (CAB, 12 kg/mol) | 2 |
| Pigment dispersion | 3 |

TABLE 11

| Non-limiting example of top coat composition of Example 9 | |
|---|---|
| Component | Amount [wt. %] |
| Acrylated epoxidized soybean oil (AESO) | 60 |
| Pyromellitic dianhydrate dimethacrylate (PMDM) | 5 |
| 2-hydroxypropyl methacrylate (HPMA) | 15 |
| Acrylated linseed oil (ALO) | 10 |
| Triethanolamine | 5 |
| Diphenyl (2,4,6-trimethylbenzoyl)phosphine oxide (TPO) | 3.5 |
| 1-hydroxycyclohexyl phenyl ketone (HCPK) | 1.5 |

TABLE 12

| Non-limiting example of top coat composition of Example 10 | |
|---|---|
| Component | Amount [wt. %] |
| Acrylated epoxidized soybean oil (AESO) | 60 |
| Hydroxyethyl methacrylate (HEMA) | <20 |
| Lauryl acrylate (LA) | 10 |

TABLE 12-continued

| Non-limiting example of top coat composition of Example 10 | |
|---|---|
| Component | Amount [wt. %] |
| Triethanolamine | 5 |
| Diphenyl (2,4,6-trimethylbenzoyl)phosphine oxide (TPO) | 3.5 |
| 1-hydroxycyclohexyl phenyl ketone (HCPK) | 1.5 |

Examples 3-10 were compared to one another regarding chip resistance, gloss, and longevity. The chip resistance and gloss were evaluated on a scale of 1 to 3, 1—poor, 2—good, 3—excellent. The examples 3-10 were further evaluated for longevity on a scale of less than or more than 7 days. The results are presented in Table 13 below.

TABLE 13

| Evaluation of Examples 3-10 | | | |
|---|---|---|---|
| Example no. | Chip resistance | Gloss | Longevity |
| 3 | 1 | 1 | <7 |
| 4 | 1 | 1 | <7 |
| 5 | 2 | 2 | <7 |
| 6 + 7 | 3 | 3 | >7 |
| 8 + 7 | 3 | 3 | >7 |
| 9 + 7 | 3 | 3 | >7 |
| 10 | 2 | 1 | <7 |

The combination of Examples 6+7 was further tested for longevity. Several samples of the system were prepared and applied onto nails. Each sample included two applications of Example 6 base+color coat and one application of Example 7 top coat on top of the base+color coat. Cure time was 45 s. The wear resistance was evaluated on a scale of 1 to 3, 1—poor, 2—good, 3—excellent. The results are presented in Table 14 below.

TABLE 14

| Wear resistance and longevity data for Samples A-H | | | | | | | | | | | | | | |
|---|---|---|---|---|---|---|---|---|---|---|---|---|---|---|
| Sample | Day No. | | | | | | | | | | | | | |
| No. | 1 | 2 | 3 | 4 | 5 | 6 | 7 | 8 | 9 | 10 | 11 | 12 | 13 | 14 |
| A | 3 | 3 | 3 | 3 | 3 | 3 | 3 | 3 | — | — | — | — | — | — |
| B | 3 | 3 | 3 | 3 | 3 | 3 | 3 | 3 | 3 | 3 | 3 | — | — | — |
| C | 3 | 3 | 3 | 3 | 3 | 3 | 3 | 3 | 3 | 3 | 3 | — | — | — |
| D | 3 | 3 | 3 | 3 | 3 | 3 | 3 | 2 | — | — | — | — | — | — |
| E | 3 | 3 | 3 | 3 | 3 | 3 | 3 | 3 | 3 | 2 | — | — | — | — |
| F | 3 | 3 | 3 | 3 | 3 | 3 | 3 | 3 | 3 | 2 | 2 | 2 | — | — |
| G | 3 | 3 | 3 | 3 | 3 | 3 | 3 | 3 | 3 | 3 | 3 | 3 | 3 | 3 |
| H | 3 | 3 | 3 | 3 | 3 | 3 | 3 | 3 | 3 | 3 | 3 | 3 | 3 | 3 |

While exemplary embodiments are described above, it is not intended that these embodiments describe all possible forms encompassed by the claims. The words used in the specification are words of description rather than limitation, and it is understood that various changes can be made without departing from the scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on specific application and implementation. These attributes can include, but are not limited to cost, strength, durability, life cycle cost, marketability, appearance, packaging size, serviceability, weight, manufacturability, ease of assembly, etc. As such to the extent any such embodiments are described as less desirable than other embodiments or prior art implementations with respect to one or more characteristics, these embodiments are not outside the scope of the disclosure and can be desirable for particular applications.

What is claimed is:

1. A nail-care composition comprising:

at least about 50 wt. % bio-based components, based on the total weight of the composition, including acrylated epoxidized soybean oil and acrylated linseed oil as bio-based monomer(s) and/or oligomer(s) in a ratio of the acrylated epoxidized soybean oil to the acrylated linseed oil of about 4:1 to 7:1 by weight, photoinitiator(s), and adhesion promoter(s) including hydroxyethyl methacrylate (HEMA)-based and/or a hydroxypropyl methacrylate (HPMA)-based monomer(s), the nail-care composition having a shear-dependent viscosity of about 1200-4000 cP, measured according to ASTM D7867, under shear stress of about 10-180 $N/m^2$.

2. The composition of claim 1, wherein the adhesion promoter(s) are bio-based.

3. The composition of claim 1, wherein the adhesion promoter(s) include at least two different compounds.

4. The composition of claim 3, wherein the at least two different compounds are in a ratio of a first adhesion promoter compound to a second adhesion promoter compound of about 1:2 to 2:1 by weight.

5. The composition of claim 1, wherein the photoinitiator(s) include two different compounds in a ratio of a first photoinitiator compound to a second initiator compound of about 3.5:1.5 by weight.

6. The composition of claim 1, further comprising a cellulose-based film former in an amount of about 1-10 wt. %, based on the total weight of the composition.

7. The composition of claim 6, wherein the cellulose-based film former includes cellulose acetate butyrate having molecular weight of at least about 12 kg/mol.

8. The composition of claim 1, further comprising an accelerator in an amount of up to about 10 wt. %, based on the total weight of the composition.

9. A nail-care composition comprising:

about 40-80 wt. % bio-based monomer and/or oligomer(s);

about 15-30 wt. % adhesion promoter(s) including hydroxyethyl methacrylate (HEMA)-based and/or hydroxypropyl methacrylate (HPMA)-based monomer(s); and about 1-7 wt. % photoinitiator(s), the nail-care composition being a thixotropic fluid with more than about 50 wt. % of the composition being bio-based and having a shear-dependent viscosity of about 1200-4000 cP, measured according to ASTM D7867, under shear stress of about 10-180 $N/m^2$.

10. The composition of claim 9, wherein the bio-based monomer and/or oligomer(s) include acrylated vegetable/plant oil(s) with a glass transition temperature $T_g$ of about −15 to 35° C., measured according to ASTM D882.

11. The composition of claim 9, wherein the adhesion promoter(s) are bio-based.

12. The composition of claim 9, wherein the photoinitiator(s) include two different compounds in a ratio of a first photoinitiator compound to a second photoinitiator compound of about 3.5:1.5 by weight.

13. The composition of claim 9, further comprising about 1-7 wt. % cellulose-based film former(s), 1-5 wt. % pigment(s), 1-10 wt. % accelerator(s), or a combination thereof, the weight % based on the total weight of the composition.

14. The composition of claim 9, wherein the applied and cured composition has an impact resistance of at least about 40 in/lbs, as measured according to ASTM D2794.

15. A nail-care system comprising:

a first thixotropic, predominantly bio-based composition, applicable onto a keratin-based substrate, the composition including:

about 50-70 wt. % bio-based monomer and/or oligomer(s) including vegetable and/or plant oils;

about 15-30 wt. % adhesion promoter(s) including hydroxyethyl methacrylate (HEMA)-based and/or hydroxypropyl methacrylate (HPMA)-based monomer(s);

about 1-10 wt. % cellulose-based film former(s); and about 1-7 wt. % initiator(s), the system, when applied and cured, has an impact resistance of at least about 40 in/lbs, as measured according to ASTM D2794 and longevity of at least 7 days.

16. The system of claim 15, further comprising a second thixotropic, predominantly bio-based composition, applicable onto the first composition after cure, the composition including:

about 50-70 wt. % bio-based monomer and/or oligomer(s) including vegetable and/or plant oils;

about 15-30 wt. % adhesion promoter(s);

about 1-7 wt. % initiator(s); and about 1-7 wt. % accelerator(s).

17. The system of claim 15, further comprising a second thixotropic, pigment-free, predominantly bio-based composition, and wherein the first composition further comprises a pigment dispersion.

18. The system of claim 17, wherein the second composition includes at least one different initiator than the first composition.

19. The system of claim 15, wherein the system is substantially free of fossil-based components.

20. The system of claim 15, wherein the vegetable and/or plant oils include a mixture of acrylated epoxidized soybean oil and acrylated linseed oil.

* * * * *